United States Patent
Austring

(10) Patent No.: US 12,182,157 B2
(45) Date of Patent: Dec. 31, 2024

(54) SYSTEM AND METHOD OF EXECUTION CONTEXT PROCESSING WITH ADDRESSABLE UNIVERSAL DATA LOCATION

(71) Applicant: Technologies IP, LLC, Fort Worth, TX (US)

(72) Inventor: Ronald Raymond Austring, English Harbour (AG)

(73) Assignee: Technologies IP, LLC, Fort Worth, TX (US)

( * ) Notice: Subject to any disclaimer, the term of this patent is extended or adjusted under 35 U.S.C. 154(b) by 0 days.

(21) Appl. No.: 17/730,384

(22) Filed: Apr. 27, 2022

(65) Prior Publication Data

US 2022/0342904 A1    Oct. 27, 2022

Related U.S. Application Data

(60) Provisional application No. 63/201,385, filed on Apr. 27, 2021, provisional application No. 63/201,387, (Continued)

(51) Int. Cl.
*G06F 16/25* (2019.01)
*G06F 16/27* (2019.01)
(Continued)

(52) U.S. Cl.
CPC ............ *G06F 16/258* (2019.01); *G06F 16/27* (2019.01); *G06F 21/6245* (2013.01);
(Continued)

(58) Field of Classification Search
CPC .... G06F 16/258; G06F 16/27; G06F 21/6245; G06F 2221/2141; G06F 16/1794;
(Continued)

(56) References Cited

U.S. PATENT DOCUMENTS

| | | |
|---|---|---|
| 7,689,998 B1 | 3/2010 | Chrysanthakopoulos |
| 8,612,363 B2 | 12/2013 | Karkanias et al. |

(Continued)

FOREIGN PATENT DOCUMENTS

WO    2019241166 A1    12/2019

OTHER PUBLICATIONS

Vogl et al. "Persistent Data-only Malware: Function Hooks without Code." NDSS. 2014. Feb. 26, 2014 (Feb. 26, 2014) Retrieved on Jul. 29, 2022 (Jul. 29, 2022).

(Continued)

*Primary Examiner* — Kris E Mackes
*Assistant Examiner* — Lin Lin M Htay
(74) *Attorney, Agent, or Firm* — Whitaker Chalk Swindle & Schwartz PLLC; Enrique Sanchez, Jr.

(57) ABSTRACT

A system and method for execution context processing with addressable universal data location that can address, process, and standardize data contained in different types of memory structures is presented. The present disclosure provides for an addressable data locator system called an Execution Context Property Path (XPP) that can access a 'property' within a 'Property Collection,' a 'property' within a graph of nested 'Property Collections,' or a 'property' within an array of 'Property Collections.' An execution context is a dynamic system that can change the processing logic and data requirements of functions at runtime by passing a 'function' a reference to an 'execution context' object and have the function retrieve the data items it needs through the 'execution context' object. For example, when new 'input data' is received on a listener, the listener can spawn a new thread and an 'execution context' object to manage the processing of the 'input data.'

16 Claims, 8 Drawing Sheets

Related U.S. Application Data filed on Apr. 27, 2021, provisional application No. 63/201,386, filed on Apr. 27, 2021, provisional application No. 63/201,388, filed on Apr. 27, 2021, provisional application No. 63/201,383, filed on Apr. 27, 2021.

(51) Int. Cl.

| | | |
|---|---|---|
| *G06F 21/62* | (2013.01) | |
| *G06Q 20/06* | (2012.01) | |
| *G06Q 20/12* | (2012.01) | |
| *G06Q 20/36* | (2012.01) | |
| *G06Q 30/0283* | (2023.01) | |
| *G16H 10/60* | (2018.01) | |
| *H04L 9/00* | (2022.01) | |

(52) U.S. Cl.
CPC ....... *G06Q 20/065* (2013.01); *G06Q 20/1235* (2013.01); *G06Q 20/367* (2013.01); *G06Q 30/0283* (2013.01); *G16H 10/60* (2018.01); *H04L 9/50* (2022.05); *G06F 2221/2141* (2013.01); *H04L 2209/56* (2013.01)

(58) Field of Classification Search
CPC ........ G06H 10/60; G04L 9/50; G06Q 20/065; G06Q 20/1235; G06Q 20/367; G06Q 30/0283; H04L 2209/56
See application file for complete search history.

(56) References Cited

U.S. PATENT DOCUMENTS

| | | | |
|---|---|---|---|
| 8,790,255 B2 | 7/2014 | Behar | |
| 9,997,082 B2 | 6/2018 | Kaleal | |
| 10,204,384 B2 | 2/2019 | Mehta et al. | |
| 10,296,297 B2* | 5/2019 | Kumar | G06F 8/31 |
| 10,373,466 B1 | 8/2019 | St Amant | |
| 10,511,580 B2 | 12/2019 | Isaacson et al. | |
| 10,643,266 B2 | 5/2020 | Isaacson et al. | |
| 10,825,111 B2 | 11/2020 | Mehta et al. | |
| 10,860,604 B1 | 12/2020 | Pandey et al. | |
| 10,898,131 B2 | 1/2021 | Iacoviello et al. | |
| 10,909,638 B2 | 2/2021 | Mehta et al. | |
| 11,080,777 B2 | 8/2021 | Isaacson et al. | |
| 11,093,911 B2 | 8/2021 | Mallampalli et al. | |
| 11,227,675 B2 | 1/2022 | Bulleit et al. | |
| 11,259,729 B2 | 3/2022 | St Amant et al. | |
| 11,354,946 B2 | 6/2022 | Pratz et al. | |
| 11,354,947 B2 | 6/2022 | Pratz et al. | |
| 11,397,728 B2 | 7/2022 | Pandey et al. | |
| 11,423,712 B2 | 8/2022 | Pratz et al. | |
| 11,522,703 B1 | 12/2022 | Jain et al. | |
| 11,657,176 B2 | 5/2023 | Bulleit et al. | |
| 11,664,099 B1 | 5/2023 | Jain et al. | |
| 11,793,725 B1 | 10/2023 | Badik et al. | |
| 11,842,380 B2 | 12/2023 | Isaacson et al. | |
| 11,903,725 B2 | 2/2024 | Iacoviello et al. | |
| 11,915,303 B2 | 2/2024 | Isaacson et al. | |
| 11,990,233 B2 | 5/2024 | Kaleal, III | |
| 2003/0101169 A1* | 5/2003 | Bhatt | G06F 16/86 |
| 2005/0273783 A1 | 12/2005 | Tankov et al. | |
| 2007/0005600 A1* | 1/2007 | Dutta | G06F 21/6218 707/999.009 |
| 2007/0255936 A1 | 11/2007 | Stemen | |
| 2010/0319001 A1 | 12/2010 | Jones | |
| 2012/0071771 A1 | 3/2012 | Behar | |
| 2012/0127157 A1 | 5/2012 | Adler et al. | |
| 2012/0182431 A1 | 7/2012 | Asanov | |
| 2012/0271143 A1 | 10/2012 | Aragones et al. | |
| 2013/0178960 A1 | 7/2013 | Sheehan et al. | |
| 2013/0252731 A1 | 9/2013 | Dugan et al. | |
| 2014/0136237 A1 | 5/2014 | Anderson et al. | |
| 2014/0188009 A1 | 7/2014 | Lange et al. | |
| 2014/0379615 A1* | 12/2014 | Brigham | G06N 3/126 706/11 |
| 2016/0004820 A1 | 1/2016 | Moore | |
| 2016/0077901 A1* | 3/2016 | Roth | G06F 8/315 719/328 |
| 2017/0161435 A1 | 6/2017 | Orosco | |
| 2017/0212783 A1* | 7/2017 | Choi | G06F 9/5061 |
| 2017/0235969 A1* | 8/2017 | Kamara | G06F 16/284 713/159 |
| 2018/0075091 A1 | 3/2018 | Weiss et al. | |
| 2018/0165416 A1 | 6/2018 | Saxena et al. | |
| 2019/0188760 A1 | 6/2019 | Ekambaram et al. | |
| 2019/0230070 A1 | 7/2019 | Isaacson et al. | |
| 2019/0306137 A1 | 10/2019 | Isaacson et al. | |
| 2019/0349426 A1* | 11/2019 | Smith | H04L 67/1093 |
| 2019/0354693 A1 | 11/2019 | Yoon et al. | |
| 2020/0012676 A1 | 1/2020 | Narang et al. | |
| 2020/0320061 A1 | 10/2020 | Korpman et al. | |
| 2020/0334032 A1 | 10/2020 | Smith | |
| 2020/0374104 A1 | 11/2020 | Heath | |
| 2020/0382480 A1 | 12/2020 | Isaacson et al. | |
| 2021/0358015 A1 | 11/2021 | Isaacson et al. | |
| 2021/0365940 A1 | 11/2021 | Tietzen et al. | |
| 2021/0375409 A1 | 12/2021 | Romantsov et al. | |
| 2021/0383335 A1 | 12/2021 | Mallampalli et al. | |
| 2022/0019366 A1 | 1/2022 | Freilich et al. | |
| 2022/0188816 A1 | 6/2022 | McFarlane | |
| 2022/0345314 A1 | 10/2022 | Doiron et al. | |
| 2023/0351474 A1 | 11/2023 | Isaacson et al. | |
| 2023/0360109 A1 | 11/2023 | Isaacson et al. | |
| 2024/0013283 A1 | 1/2024 | Isaacson et al. | |
| 2024/0113728 A1 | 4/2024 | Cooper et al. | |

OTHER PUBLICATIONS

PCT International Application No. PCT/US2022/026457, International Search Report and Written Opinion, dated Aug. 19, 2022, 8 pages.
PCT International Appl. No. PCT/US22/26593 International Search Report and Written Opinion, 7 pages, mailed Aug. 26, 2022.
Zhang et al., FHIRChain: Applying Blockchain to Securely and Scalably Share Clinical Data, 2018, p. 267-278, Elsevier.

* cited by examiner

SYSTEM AND METHOD OF EXECUTION CONTEXT PROCESSING WITH ADDRESSABLE UNIVERSAL DATA LOCATION

CROSS-REFERENCE TO RELATED APPLICATIONS

The present application claims priority to U.S. Provisional Patent Application Ser. No. 63/201,383, filed on Apr. 27, 2021, entitled "ADDRESSABLE UNIVERSAL DATA LOCATOR SYSTEM FOR PROGRAM EXECUTION AND METHOD THEREFOR," U.S. Provisional Patent Application Ser. No. 63/201,385, filed on Apr. 27, 2021, entitled "ELECTRONIC HEALTH RECORD PERMISSIONING SYSTEM AND METHOD," U.S. Provisional Patent Application Ser. No. 63/201,388, filed on Apr. 27, 2021, entitled "ELECTRONIC HEALTH RECORD DATA QUALIFICATION SYSTEM AND METHOD," U.S. Provisional Patent Application Ser. No. 63/201,387, filed on Apr. 27, 2021, entitled "SERVER PROTOCOL FORMATTING SYSTEM AND METHOD," and U.S. Provisional Patent Application Ser. No. 63/201,386, filed on Apr. 27, 2021, entitled "PROPERTY COLLECTION SYSTEM AND METHOD," the contents of which are incorporated herein in their entireties for all purposes.

TECHNICAL FIELD

The present disclosure relates generally to data storage and retrieval. More specifically, in certain embodiments, the present disclosure relates to a system and method for addressing and processing data contained in different types of memory structures.

BACKGROUND

A typical programming technique is to pass information to methods/functions as arguments. This requires that the code calling the function gather all the data required by the function and then pass that data to the function using the arguments of the function. The arguments position, name, and data type, for a specific method/function form what is known as the method/function signature. The calling program must know about the signature of the method/function to be called. This results in a tight coupling between the caller of the function and the function. A major weakness of function arguments is that the caller must know where to get the data to provide to the function, and if new data is required by the method/function the signature changes and breaks all callers. The function signature prevents new data inputs from being added, without breaking the caller.

Data is traditionally stored in databases or in a memory, such as a hard drive. In order to access the data, typically a directory path to the data is required to identify the location where the data is stored. A Uniform Resource Identifier (URI) is a unique sequence of characters that identifies a logical or physical resource used by web technologies. URIs may be used to identify anything, including real-world objects, such as people and places, concepts, or information resources such as web pages and books. Some URIs provide a means of locating and retrieving information resources on a network (either on the Internet or on another private network, such as a computer filesystem or an Intranet), these are Uniform Resource Locators (URLs). Other URIs provide only a unique name, without a means of locating or retrieving the resource or information about it, these are Uniform Resource Names (URNs). The web technologies that use URIs are not limited to web browsers. URIs are used to identify anything described using the Resource Description Framework (RDF), for example, concepts that are part of an ontology defined using the Web Ontology Language (OWL), and people who are described using the Friend of a Friend vocabulary would each have an individual URI.

In traditional applications, including the technologies discussed in this background, data is contained in different types of memory structures. Accordingly, there exists a technological problem of tight coupling between the caller of the function and the function such that the caller must know where to get the data to provide to the function, coupled with no common method to address, access, and serialize data, that conventional solutions cannot solve.

SUMMARY

The present disclosure achieves technical advantages as a system and method for execution context processing with addressable universal data location that can address, process, and standardize data contained in different types of memory structures. The present disclosure provides for a system integrated into a practical application with meaningful limitations as an addressable data locator system called an Execution Context Property Path (XPP) that can access a 'property' within a 'Property Collection,' a 'property' within a graph of nested 'Property Collections,' or a 'property' within an array of 'Property Collections.' In one embodiment, an XPP can be an ascii string consisting of several components to address a 'property.' For example, the XPP can be formatted according to the following structure: <property collection><property path><query string>. The XPP can be used in association with an 'execution context' object. The execution context is a dynamic system that can change the processing logic and data requirements of functions at runtime by passing a 'function' a reference to an 'execution context' object and have the function retrieve the data items it needs through the 'execution context' object. For example, when new 'input data' is received on a listener, the listener can spawn a new thread and an 'execution context' object to manage the processing of the 'input data.' Within an application there may exist several threads of execution. Within each thread of execution the 'execution context' object can be used to manage data for the current processing thread. Within applications, 'Property Collections' can be used to represent/contain several different types of data. Almost all types of data can be stored and accessed using a 'Property Collection.' For example; images, data entities (e.g., Patient, Physician, Prescriber, Pharmacy, etc.), industry standard telecommunication standards (e.g., NCPDP, CPhA, X12 billing formats, etc.) can all be represented as a 'Property Collection' or exposed through a 'Property Collection Interface.'

The present disclosure solves the technological problem of no standardized method to address, access, and serialize the data, by at least providing an 'execution process' that defines a unique way of processing data received from a client and responding back to the client that greatly simplifies the process of saving and restoring a 'state' when 'phase' changes are occurring. The XPP can provide an addressing system to access specific data. The 'execution context' and the XPP can work together to solve the aforementioned technological problem to provide a standardized method to address, access, and serialize data. Accordingly, the claims herein are necessarily rooted in computer technology as they overcome a problem arising in the realm of computer database storage and access.

The present disclosure provides a technological solution missing from conventional systems by providing a standardized access methodology for the data and a known and predictable way to persist data (e.g., serialization). For example, Property Collections can be used to encapsulate several different types of data. This allows for a standard packaging methodology for the data. Further, as part of the execution context, the system can implement a 'listener' to generate a new thread and an 'execution context' object to manage the processing of the 'input data,' and a 'responder' to transmit 'output data' to a client.

Accordingly, the present disclosure discloses concepts inextricably tied to computer technology such that the present disclosure provides the technological benefit of distributing a computer's processing power and provide isolation for different application processes via the 'execution context' which can spawn one or more threads. The present disclosure technologically surpasses conventional technology as, during the life of a thread, the execution context can be used to create, update, delete and access 'Property Collections' stored in computer memory. Within a transaction processing environment, a thread and an associated execution context can be created when a 'transmission' is received on a listener.

It is an object of the invention to provide a system for managing data using an execution context. It is a further object of the invention to provide a method of managing data using an execution context. These and other objects are provided by the present disclosure, including at least the following embodiments.

In one embodiment, a system for managing data using an execution context, can include: a memory storing one or more property collections; and a computer processor operably coupled to the memory and capable of executing machine-readable instructions to perform program steps, the program steps comprising: receiving input data from a client, the input data having an input data format with data fields and respective data field values; instantiating a first thread; instantiating an execution context in the first thread; parsing the input data using an input parser based on the first data format; storing the parsed data in a first property collection in a standardized format to provide access to the parsed data; loading rules, rule properties, and qualifiers based upon the input data; qualifying the rules and rule properties to determine which rule properties to use for each rule; executing the rules against one or more stored property collections to generate output data; and storing the output data in an output property collection. Wherein an input parser factory determines the input parser format based on the first data format. Wherein the input data is received from the client via a listener configured to instantiate the input parser factory. Further comprising instantiating an output parser to format the output data in the input data format. Wherein the output parser factory determines the output parser format based on the input data format. Further comprising transmitting the output data in the input data format to a client. Wherein a responder transmits the output data in the input data format to a client using the same manner of transmission. Wherein the execution context addresses data using an execution context property path (XPP). Wherein the XPP is an ASCII string. Wherein the XPP includes a modifier to append additional information to an XPP request.

In another embodiment, a method of managing data using an execution context, can include: receiving input data from a client, the input data having an input data format with data fields and respective data field values; instantiating a first thread; instantiating an execution context in the first thread; parsing the input data using an input parser based on the first data format; storing the parsed data in a first property collection in a standardized format to provide access to the parsed data; loading rules, rule properties, and qualifiers based upon the input data; qualifying the rules and rule properties to determine which rule properties to use for each rule; executing the rules against one or more stored property collections to generate output data; and storing the output data in an output property collection. Wherein an input parser factory determines the input parser format based on the first data format. Wherein the input data is received from the client via a listener configured to instantiate the input parser factory. Further comprising instantiating an output parser to format the output data in the input data format. Wherein the output parser factory determines the output parser format based on the input data format. Further comprising transmitting the output data in the input data format to a client. Wherein a responder transmits the output data in the input data format to a client using the same manner of transmission. Wherein the execution context addresses data using an execution context property path (XPP). Wherein the XPP is an ASCII string. Wherein the XPP includes a modifier to append additional information to an XPP request.

BRIEF DESCRIPTION OF THE DRAWINGS

The present disclosure will be readily understood by the following detailed description, taken in conjunction with the accompanying drawings that illustrate, by way of example, the principles of the present disclosure. The drawings illustrate the design and utility of one or more embodiments of the present disclosure, in which like elements are referred to by like reference numbers or symbols. The objects and elements in the drawings are not necessarily drawn to scale, proportion, or precise positional relationship. Instead, emphasis is focused on illustrating the principles of the present disclosure.

DETAILED DESCRIPTION

The disclosure presented in the following written description and the various features and advantageous details thereof, are explained more fully with reference to the non-limiting examples included in the accompanying drawings and as detailed in the description. Descriptions of well-known components have been omitted to not unnecessarily obscure the principal features described herein. The examples used in the following description are intended to facilitate an understanding of the ways in which the disclosure can be implemented and practiced. A person of ordinary skill in the art would read this disclosure to mean that any suitable combination of the functionality or exemplary embodiments below could be combined to achieve the subject matter claimed. The disclosure includes either a representative number of species falling within the scope of the genus or structural features common to the members of the genus so that one of ordinary skill in the art can recognize the members of the genus. Accordingly, these examples should not be construed as limiting the scope of the claims.

A person of ordinary skill in the art would understand that any system claims presented herein encompass all of the elements and limitations disclosed therein, and as such, require that each system claim be viewed as a whole. Any reasonably foreseeable items functionally related to the claims are also relevant. Pursuant to Section 904 of the Manual of Patent Examination Procedure, the Examiner, after having obtained a thorough understanding of the invention disclosed and claimed in the nonprovisional application has searched the prior art as disclosed in patents and other published documents, i.e., nonpatent literature. Therefore, as evidenced by the issuance of this patent, the prior art fails to disclose or teach the elements and limitations presented in the claims as enabled by the specification and drawings, such that the presented claims are patentable under 35 U.S.C. §§ 101, 102, 103, and 112.

Figure 1:
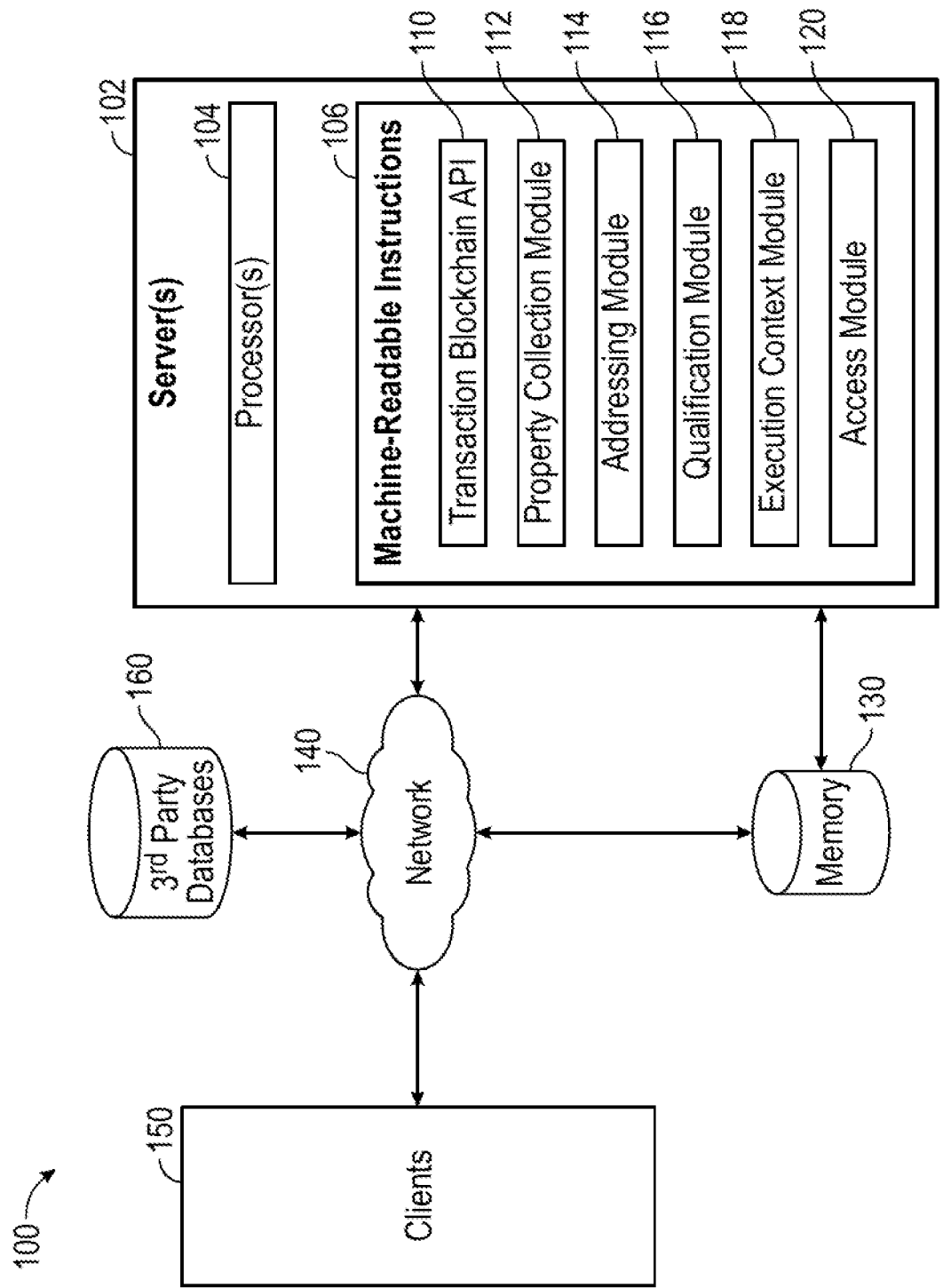
FIG. 1 illustrates an execution context system schematic, in accordance with one or more exemplary embodiments of the present disclosure.

FIG. 1 illustrates an execution context system 100 schematic, in accordance with one or more exemplary embodiments of the present disclosure. The system 100 can include one or more servers 102 having one or more processors 104, a memory 130, machine readable instructions 106, including transaction blockchain API 110, a property collection module 112, an addressing module 114, a qualification module 116, execution context module 118, and an access module 120, among other relevant modules. The server 102 can be operably coupled to one or more clients 150 via a network 140. The clients can be a physical device (e.g., mobile phone, laptop, tablet, desktop computer, wearable device, or other suitable device), program, or application. In another embodiment, a client can include a mobile phone having a mobile application configured to communicate with the server 102 over the network 140.

The aforementioned systems, components, and modules can be communicably coupled to each other via the network 140, such that data can be transmitted therebetween. The network 140 can be the Internet, intranet, computer bus, or other suitable network. The data transmission can be encrypted, unencrypted, over a VPN tunnel, or other suitable communication means. The network 140 can be a WAN, LAN, PAN, or other suitable network type. The network communication can be encrypted using PGP, Blowfish, Twofish, AES, 3DES, HTTPS, or other suitable encryption. The system 100 can be configured to provide communication via the various systems, components, and modules disclosed herein via an application programming interface (API), PCI, PCI-Express, ANSI-X12, Ethernet, Fiber, Wi-Fi, Bluetooth, or other suitable communication protocol or medium. Additionally, third party systems and databases 160 can be operably coupled to the system components via the network 140.

The data transmitted to and from the components of system 100 (e.g., the server 102, memory 130, and clients 150), can include any format, including the XPP format disclosed herein, JavaScript Object Notation (JSON), TCP/IP, XML, HTML, ASCII, SMS, CSV, representational state transfer (REST), or other suitable format. The data transmission can include a message, flag, header, header properties, metadata, and/or a body, or be encapsulated and packetized by any suitable format having same.

The server(s) 102 can be implemented in hardware, software, or a suitable combination of hardware and software therefor, and may comprise one or more software systems operating on one or more servers, having one or more processors 104, with access to memory 130. Server(s) 102 can include electronic storage, one or more processors, and/or other components. Server(s) 102 can include communication lines, connections, and/or ports to enable the exchange of information via a network 140 and/or other computing platforms. Server(s) 102 can also include a plurality of hardware, software, and/or firmware components operating together to provide the functionality attributed herein to server(s) 102. For example, server(s) 102 can be implemented by a cloud of computing platforms operating together as server(s) 102, including Software-as-a-Service (SaaS) and Platform-as-a-Service (PaaS) functionality. Additionally, the server(s) 102 can include memory 130, locally attached, network attached, or both.

Memory 130 can comprise electronic storage that can include non-transitory storage media that electronically stores information. The electronic storage media of electronic storage can include one or both of system storage that can be provided integrally (e.g., substantially non-removable) with server(s) 102 and/or removable storage that can be removably connectable to server(s) 102 via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage may include one or more virtual storage resources (e.g., cloud storage, a virtual private network, and/or other virtual storage resources). The electronic storage can include a database, or public or private distributed ledger (e.g., blockchain). Electronic storage can store machine-readable instructions 106, software algorithms, control logic, data generated by processor(s), data received from server(s), data received from computing platform(s), and/or other data that can enable server(s) to function as described herein. The electronic storage can also include third-party databases accessible via the network 140.

Processor(s) 104 can be configured to provide data processing capabilities in server(s) 102. As such, processor(s) 104 can include one or more of a digital processor, an analog processor, a digital circuit designed to process information, an analog circuit designed to process information, a state machine, and/or other mechanisms for electronically processing information, such as FPGAs or ASICs. The processor(s) 104 can be a single entity or include a plurality of processing units. These processing units can be physically located within the same device, or processor(s) 104 can represent processing functionality of a plurality of devices or software functionality operating alone, or in concert.

The processor(s) 104 can be configured to execute machine-readable instructions 106 or machine learning modules via software, hardware, firmware, some combination of software, hardware, and/or firmware, and/or other mechanisms for configuring processing capabilities on processor(s) 104. As used herein, the term "machine-readable instructions" can refer to any component or set of components that perform the functionality attributed to the machine-readable instructions component 106. This can include one or more physical processors 104 during execution of processor-readable instructions, the processor-readable instructions, circuitry, hardware, storage media, or any other components.

The server(s) 102 can be configured with machine-readable instructions having one or more functional modules. The machine-readable instructions 106 can be implemented on one or more servers 102, having one or more processors 104, with access to memory 130. The machine-readable instructions 106 can be a single networked node, or a machine cluster, which can include a distributed architecture of a plurality of networked nodes. The machine-readable instructions 106 can include control logic for implementing various functionality, as described in more detail below. The machine-readable instructions 106 can include certain functionality associated with the system 100. Additionally, the machine-readable instructions 106 can include a smart contract or multi-signature contract that can process, read, and write data to the memory 130, 3rd party database 160, including a database, distributed ledger, or blockchain.

Figure 2:
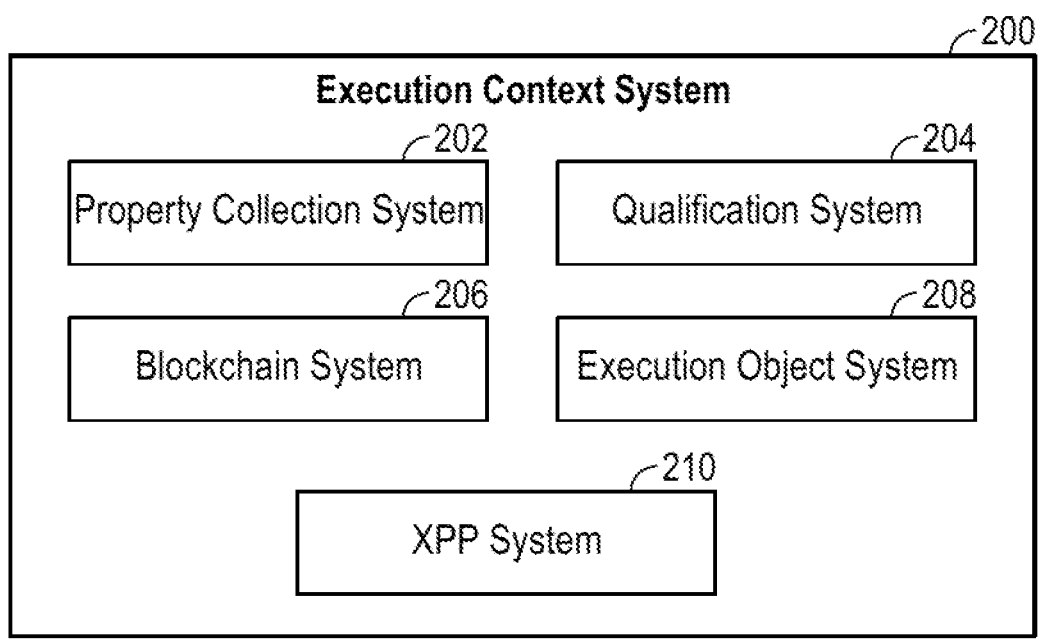
FIG. 2 illustrates a block diagram of an execution context system, in accordance with one or more exemplary embodiments of the present disclosure.

FIG. 2 illustrates a schematic view of an execution context system 200, in accordance with one or more exemplary embodiments of the present disclosure. The execution context system 200 can include a property collection system 202, a qualification system 204, a blockchain system 206, and an execution context object system 208, and an execution context property path (XPP) system 210. The execution context system 200 can be implemented on the server 102, client 150, or a suitable combination thereof. The execution context system 200 can be used to implement one or more aspects of the present disclosure.

The Property Collection system 202 can generate, manage, and access one or more Property Collections. A Property Collection can be a data encapsulation, addressing, access and persistence technology. In one embodiment, the Property Collection system 202 can provide the ability to package, access, persist and load data. For example, the Property Collection can incorporate one or more technologies, such as XML and JSON libraries, Google Protocol Buffers, or other suitable technology. In another embodiment, a 'Property Collection' can define an 'in-memory' structure and access technology that has no standard persisted form such as JSON or XML, but can be persisted to any of these formats, including rows in a database table, binary large object block, etc. In another embodiment, a 'Property Collection' can be an 'in-memory' representation, such as, for example, 'protocol buffers' that can be serialized into an efficient binary byte array such that it can be efficiently transferred via a communication channel, persisted to cache, and/or an immutable storage system, among others. In another embodiment, the Property Collection system 202 can address and access data using an XPP.

Property Collections can be used to encapsulate all or a portion of data used by an application, such as:
  Application configuration data
  Listener configuration data
  Rule Property data
  Qualifier List data
  Input data
  Entity data
  Outcome data
  Log data
  Phase data
  Report data
  Breadcrumb data The qualification system 204 can determine which business logic (rules) should be executed, and the 'property values' to use when executing the rules. This determination can be based on any data contained in 'Property Collections' managed by the 'execution context', such as: the 'input data' received from the client, 'application configuration data', 'listener configuration data', 'entities' (e.g., Patient, Pharmacy, Drug, etc.) that are loaded based on data in the current context, etc. In another embodiment, the qualification system 204 can address and access data using an XPP.

The blockchain system 206 can store, manage, and provide access to a blockchain. In one embodiment, the blockchain can be implemented on one or more platforms, including BigChainDB, nChain, Ethereum, Hyperledger, R3, Ripple, EOS, or other suitable blockchain platform. The blockchain can be a public blockchain, accessible to the general public, or a private blockchain, accessible only by those parties credentialed for access. In another embodiment, the blockchain system 206 can include a transaction blockchain API 110 for accessing the blockchain, the transaction blockchain API 110 having an interface that defines interactions between multiple components. For example, the transaction blockchain API 110 can define the kinds of calls or requests that can be made, how to make them, the data formats that should be used, the conventions to follow, and other suitable functionality related to a blockchain. In another embodiment, the transaction blockchain API 110 can access and retrieve Property Collections. In another embodiment, the blockchain system 206 can address and access data using an XPP, including data on the blockchain.

The execution context object system 208 can spawn one or more execution objects in accordance with the principles of this disclosure and as discussed in more detail below. An 'execution context' can be used extensively in multi-threaded applications. The execution context object system 208 can instantiate an 'execution context' object that can incorporate other technologies to work together to form an 'execution process', which can dictate the high-level structure of how applications are written and how they execute. The life cycle of 'Property Collections' can be managed within an 'execution context.' In one embodiment, an Execution Context can exist within a thread of an application process to manage data, data access, qualification, and execution of application logic. In another embodiment, the execution context object system 208 can address, process, and access data using an XPP.

The execution context property path (XPP) system 210 can provide for data access and addressing of one or more data elements in the system in a reliable and standardized way. In one embodiment, an XPP can be a modified form of a Uniform Resource Identifier (URI) used to address and access a 'property' within a 'Property Collection' being managed by the 'Execution Context.' An XPP can be used to locate a specific 'Property Collection' and access a 'property' within that collection. In another embodiment, an XPP can be an ascii string. For example, an XPP can consists of several components used to address a 'property': <property collection><property path><query string>. In ASCII string form, the XPP can be stored as data and provided from a source external to the application. Particularly, an XPP as an ASCII string (with the proper encoding) can be used to communicate the location of any single piece of data or a collection of data within an application program. Accordingly, the XPP for a particular data structure can be copied, pasted, printed, emailed, sent in an instance messaging program, included as part of the content exposed by another XPP, etc. In another embodiment, An XPP can be used within an 'execution context' to access a 'property' within a 'Property Collection', a 'property' within a graph of nested 'Property Collections,' or a 'property' within an array of 'Property Collections.' A 'Qualification List' is an example of how an XPP can be stored within external data but loaded into an application and used to retrieve a specific data item from a known 'Property Collection,' as discussed in more detail herein. In another embodiment, the XPP system 210 can address, process, and access data using an XPP.

Figure 3:
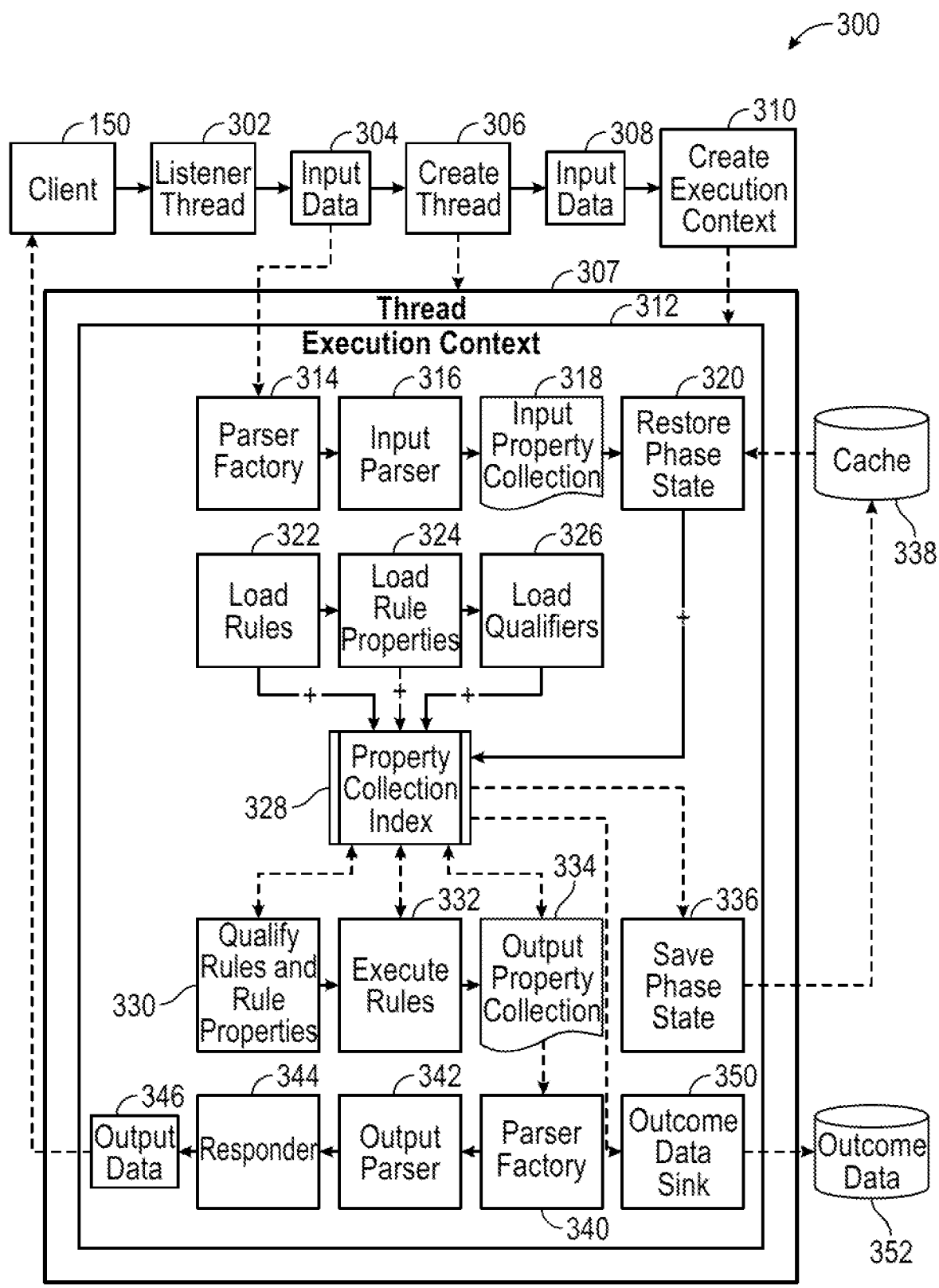
FIG. 3 illustrates a schematic exemplifying an execution process, in accordance with one or more exemplary embodiments of the present disclosure.

Referring to FIG. 3, there is shown a schematic view of an 'execution process,' 300, in accordance with one or more embodiments of the present disclosure. In one embodiment, an 'execution process' can define a unique way of processing data received from a client and responding back to the client. This 'process' can be managed by what it is referred to as the 'execution context' object.

In one embodiment, during the 'execution process' 300, data can be read from and written to one or more 'Property Collections.' In normal applications, data is contained in different types of memory structures with no common method to address, access, and serialize the data. Conforming the data with a standardized framework greatly simplifies the process of saving and restoring 'state' when 'phase' changes are occurring. The following technology components can be used by the process: Property Collection, XPP, and Execution Context, among others.

The execution process 300 can be executed via control logic that can be implemented as an algorithm on a general-purpose computing platform or other suitable microprocessor-based system. The control logic can be achieved with software, hardware, an application programming interface (API), a network connection, a network transfer protocol, HTML, DHTML, JavaScript, Dojo, Ruby, Rails, other suitable applications, or a suitable combination thereof.

The control logic can leverage the ability of a computer platform to spawn multiple processes and threads by processing entries, requests, and attempts in a database simultaneously. The speed and efficiency of the control logic can be greatly improved by instantiating more than one process at one time. However, one skilled in the art of programming will appreciate that use of a single processing thread can also be utilized and is within the scope of the present disclosure.

In one embodiment, a client 150 can be operably coupled to (or include) a listener 302 configured to generate input data 304, create thread logic 306 configured to spawn an 'execution process' thread 307, input data 308 generated by the create thread logic 306, and create execution context logic 306 configured to spawn an 'execution context' object 312 in the thread 307. When an 'execution context' object 310 is created it receives new 'input data' 304 to be processed. The execution context 312 can read and write data to memory 338 (e.g., cache, database, blockchain, etc.) and store outcome data 352 or transmit output data 346 back to the client 150. The following describes a high-level exemplary embodiment of the control logic processing steps of the 'execution context' once this occurs:

The 'execution context' object 310 can determine if the 'listener' 302 has an associated 'parser factory' object 314 defined.

If the 'listener' 302 has an associated 'parser factory' object 314 defined, a parser factory object 314 can be instantiated and the 'input data' 304 can be passed to the parser factory object 314 for analysis. Based on the 'input data' format, the parser factory 314 determines and instantiates the correct input parser 316. As the input data can take many different formats, the instantiated input parser is selected by the control logic to properly extract the relevant data fields and associated field values. For example, the input data can be in a format associated with an oracle database, a blockchain, a spreadsheet, CSV file, an email, a user interface post form, or other suitable format. The parser 316 can process the 'input data' 304 and either create and populate a 'Property Collection' object or provide a 'Property Collection Interface', or otherwise input 318 a Property Collection to represent the received 'input data' 304 as a 'Property Collection.'

If the 'listener' 302 does not have an associated 'parser factory' object 314 defined, the 'execution context' 312 identifies that it is receiving a 'Property Collection' and deserializes the collection into a 'Property Collection' object.

Based on the type of 'parser' 316 instantiated and the 'type' of input data 304 that the parser 316 represents, the 'execution context' 312 can determine the 'phase' of the 'input data' 304.

This 'Property Collection' or 'Property Collection Interface', representing the 'input data' 304 is added to the 'execution context property collection index' 328 and typically named as '<phase>.Request' (e.g., where <phase> is an integer that represents the current phase).

If the 'phase' of the 'input data' implies a previous phase was processed the 'execution context' associated with the previous phase will be restored 320. This process can restore the state of all 'Property Collections' as they existed at the end of the previous phase.

The 'execution context' can then determine and load the 'rules' 322 that should be executed based on the type of 'input data' 304 received and the current 'phase' of the input data 304.

Once the 'rules' have been determined, they are sorted into a sequential processing list. For example, the rules can be sorted by priority and loaded 324.

The 'execution context' object can then process each rule as follows:

Load qualifiers 326 and perform qualification 330 (e.g., using predefined 'Qualification Lists' and 'Qualification Functions'), which can determine and load a list of 'rule properties' that qualify based on the 'type', 'phase', content of the 'input data', and/or property values with an 'entity' referenced by the 'input data'.

Once a list of the 'rule properties' have been determined, through qualification, the 'rule' can execute 332 once for each 'rule—property collection' in the array of 'rule—property collection' instances. For example, the rules and rule properties can identify the fields and respective values that are to be matched, or thresholds of field values that can be matched, with stored 'Property Collections.' Additionally, the rules and rule properties can identify the "property Collections" and/or phases to search, among other criteria.

The 'rule properties' can be used to supply additional information to the rule so that it can customize its execution based on these properties.

As a 'Rule' is executed it may choose to load additional data items/entities (e.g., Patient, Pharmacy, etc.) from some kind of persistence media, such as a database, cache, etc. These data items/entities can be added as 'Property Collections' to the 'execution context property collection index' and can be available to other 'Rules' and 'Qualifiers' using an XPP.

Once all rules have completed processing the execution context: determines the 'output data' to be sent back to the client and generates and output property collection 334; determines the mechanism of how the 'output data' will be sent back to the client (e.g., typically the same way it was received); and determines if the 'listener' has an associated 'parser factory' 340 defined.

If the 'listener' 302 has an associated 'parser factory' 314 defined: the parser factory 340 can be used to create an associated output 'response parser' 342; the 'Property Collection' can be used as the 'output data' and loaded into the 'response parser' 342 and the parser creates the 'output data' 346 to be sent back to the client 150; and send the 'output data' 346 to a preconfigured responder 344, which sends it to the 'client' 150.

If the 'listener' 302 does not have an associated 'parser factory' 314 defined: the 'Property Collection' being used to represent the 'output data' can be serialized into a 'byte array;' sends the 'byte array' to a preconfigured responder, which sends it to the 'client' 150; determines if additional phases and/or types of 'input data' are expected and saves the phase state 336—if so, the current 'execution context' object is persisted to memory 338 (e.g., cache) where it can be retrieved when 'input data' 304 is received that is associated with the next phase of processing; and sends all accumulated 'outcome data' to a preconfigured 'outcome data sink' 350 for saving in an outcome data storage 352. The responder can transmit the output data in the input data format to a client using the same manner of transmission. For example, if the client transmitted the data via a user interface, the same user interface can be used to transmit the output data to the client. If the output data was transmitted using email, the output data can be transmitted using email, and so on.

In another embodiment, an application can be a set of predefined services. As the name implies a 'service' provides a service to the application. The 'service' can be 'started,' 'paused,' and 'stopped'. When 'started,' a 'service' creates a 'thread', obtains or allocates any resources it needs and performs its services within that thread. When 'paused' a 'service' stops providing its services until it is 'started' again. When 'stopped', a 'service', releases the resources it has obtained, and exits the thread, which results in the threads termination.

In another embodiment, within an application, one of the 'services' can configure and start preconfigured 'listeners,' which can 'listen' for 'input data.' Within an application, different types of 'listeners' can be configured that 'listen' for 'input data' from a variety of sources. Exemplary listeners can include:

A user interface, hosted in a stand-alone application or a web-page;
A 'file' listener, which monitors a specific folder for new file(s) dropped into the folder;
A 'message queue' listener, which monitors a message queue for new messages;
A 'database' listener, which monitors a database table for new data rows;
A 'HTTP(S)' listener, which monitors an http endpoint for new 'transmissions;' and
A 'TCP/IP socket' listener, which monitors a socket port for new 'transmissions.'

When new 'input data' is received on a listener, the listener can create a new thread and an 'execution context' object to manage the processing of the 'input data'.

In one embodiment, a 'responder' can be used to send 'output data' to a client. For example, the 'output data' can be a simple acknowledgement or a complex data structure. A 'responder' can be optional and configured as part of the listener. The 'responder type' does not need to be related to the 'listener type.' For example, a 'listener' can be configured to receive 'input data' via a 'message queue,' but respond back to the client using an HTTP connection.

As the 'execution process' executes, it may generate information such as log data, breadcrumb data, reporting data, phase data, result data, smart contract data, or other suitable information. This information can be referred to as 'outcome data' and can be sent to an 'outcome data sink' 352 at the end of each phase of processing.

Within each thread of execution created to process 'input data', an 'execution context' object can be instantiated with control logic configured to:

managing the processing flow
managing the life cycle and access to 'Property Collections'
persisting and restoring 'Property Collections', during phase changes
loading application logic, known as rules
loading rule properties
loading 'qualification lists', and 'qualification logic'
qualifying rules and rule properties
executing rules
responding back to the client
sending 'outcome data' to an 'outcome data sink'

During the life of a thread, the 'execution context' can be used to create, update, delete and access 'Property Collections.' Almost all data used by the 'execution context' can be stored in a 'Property Collection.'

Figure 4:
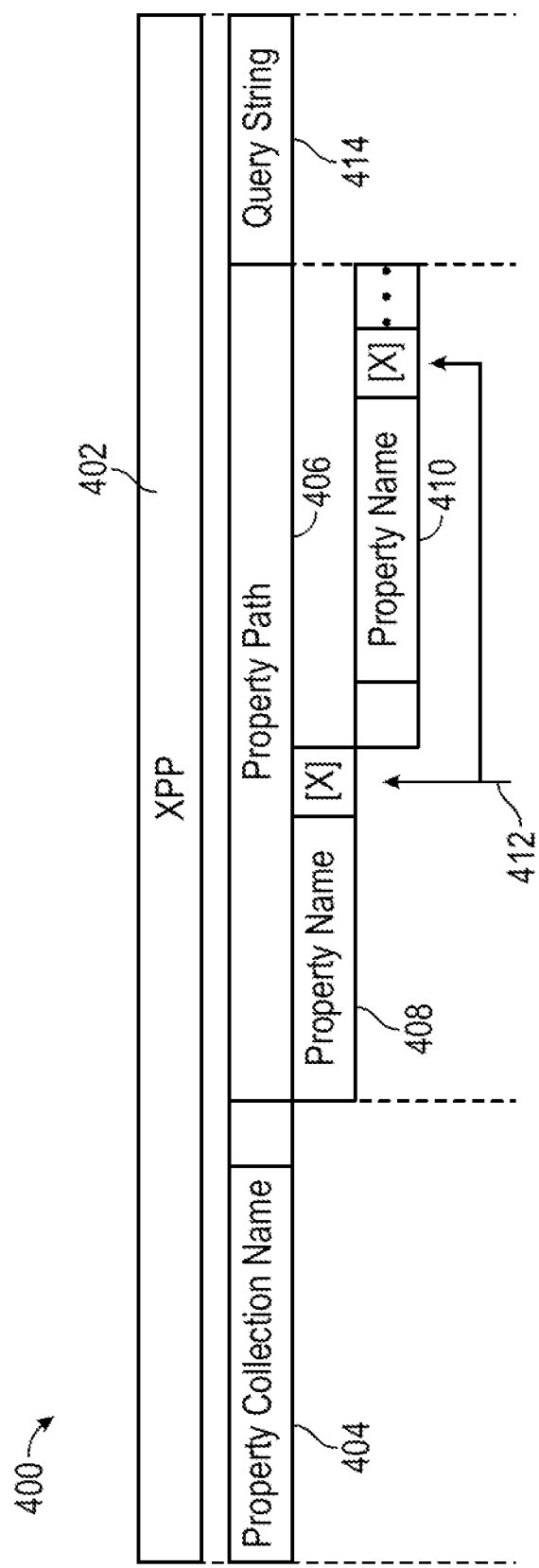
FIG. 4 illustrates a diagram of an execution context property path format, in accordance with one or more exemplary embodiments of the present disclosure.

FIG. 4 shows a schematic of an Execution Context Property Path (XPP), in accordance with one or more embodiments of the present disclosure. In one embodiment, to communicate the location of any single piece of data or a collection of data within an application program, a data item, within an application program, can package itself within a 'Property Collection' and register that 'Property Collection' with the 'execution context.' Another benefit of having all data within an application registered, and addressable, is that the current state of an 'execution context' can be saved (e.g., and later restored), simply by setting all the 'Property Collections' to persist their contents to some kind of storage medium (cache, database, flat file, etc.). At some time in the future, to restore the 'execution context', the 'Property Collections' can simply be read back from the storage medium.

An XPP is similar to a 'property path', but the first 'name' in the 'property path', is the name of a 'property collection'. An XPP might only be used in association with an 'execution context.' In general, an XPP is a technology that provides a consistent way to address and access 'Property Collection' data within an 'execution context' of an application. For example, to access the 'Name' property of the 'Patient' property collection, the XPP could be: "Patient.Name." If referencing a 'nested' property collection, the XPP can begin with the name of the 'Property Collection' (e.g., 'Patient'), following by the 'property path' that forms the address of the nested property (e.g., Patient.Address.Zip).

In one embodiment, the 'execution context' can also support 'property access methods' for each data type supported by property collections. As a minimum, these methods accept an XPP as an argument and can be used to read (e.g., get) and write (e.g., put) property values. The execution context can also support a method used to retrieve a 'property value' as an 'object.' This retrieval method can used by the 'qualification engine' when data types are discovered at 'runtime.' Examples of 'put' and 'get' property types are shown below:

Get Property Value

| Property Type | Method Name |
| --- | --- |
| String | getPropertyValueAsString |
| SByte | getPropertyValueAsSInt08 |
| Byte | getPropertyValueAsUInt08 |
| Int16 | getPropertyValueAs SInt16 |
| UInt16 | getPropertyValueAsUInt16 |
| Int32 | getPropertyValueAs SInt32 |
| UInt32 | getPropertyValueAsUInt32 |
| Int64 | getPropertyValueAsInt64 |
| UInt64 | getPropertyValueAsUInt64 |
| Decimal | getPropertyValueAsDecimal |
| Boolean | getPropertyValueAsBoolean |
| UInt32 | getPropertyValueAsDate |
| UInt32 | getPropertyValueAsTime |
| UInt64 | getPropertyValueAsDateTime |
| Byte[ ] | getPropertyValueAsByteArray |
| Object | getPropertyValueAsObject |
| List <ITpePropertyCollection> | getPropertyValueAsArrayOfPropertyCollections |

Put Property Value

| Property Type | Method Name |
| --- | --- |
| String | putPropertyValueAsString |
| SByte | putPropertyValueAsSInt08 |
| Byte | putPropertyValueAsUInt08 |
| Int16 | putPropertyValueAsSInt16 |
| UInt16 | putPropertyValueAsUInt16 |
| Int32 | putPropertyValueAsSInt32 |
| UInt32 | putPropertyValueAsUInt32 |
| Int64 | putPropertyValueAsInt64 |
| UInt64 | putPropertyValueAsUInt64 |
| Decimal | putPropertyValueAsDecimal |
| Boolean | putPropertyValueAsBoolean |
| UInt32 | putPropertyValueAsDate |
| UInt32 | putPropertyValueAsTime |
| UInt64 | putPropertyValueAsDateTime |
| Byte[ ] | putPropertyValueAsByteArray |

In another exemplary embodiment, XPP requests can go through an 'execution context' and access a 'property' within a 'Property Collection' or nested 'Property Collection'. A 'property value' may be a 'String', 'Integer, 'Decimal', 'Boolean', 'Date', 'Time', 'DateTime', a 'Byte Array' a 'property collection reference', or an array of 'property collection references'. An XPP can use dot notation (.) to form an address to a 'property.' The first name of an XPP can be the name of a 'property collection' (e.g., 'Patient'), followed by a 'property path'. For example: 'Patient.Address.Zip'. An XPP is used by the 'Data Access Methods' on the 'execution context. These methods can be used to get (e.g., read data) and put (e.g., write data), to 'Property Collections'.

Additionally, an XPP can allow for the use of modifiers. A 'modifier' can be used to append additional information to an XPP request. An example of a modifier can be: "Request.NDC?Type=string".

The modifier above can inform an XPP manager to return the NDC as a 'string' value. Modifiers are normally used within the 'qualification engine' to transform a 'property value' to a specific data type. Modifiers are rarely used when using the data access methods to get a 'property value.' This technique can be used extensively in 'multi-phase transaction processing' systems. See, e.g., FIG. 5.

Figure 5:
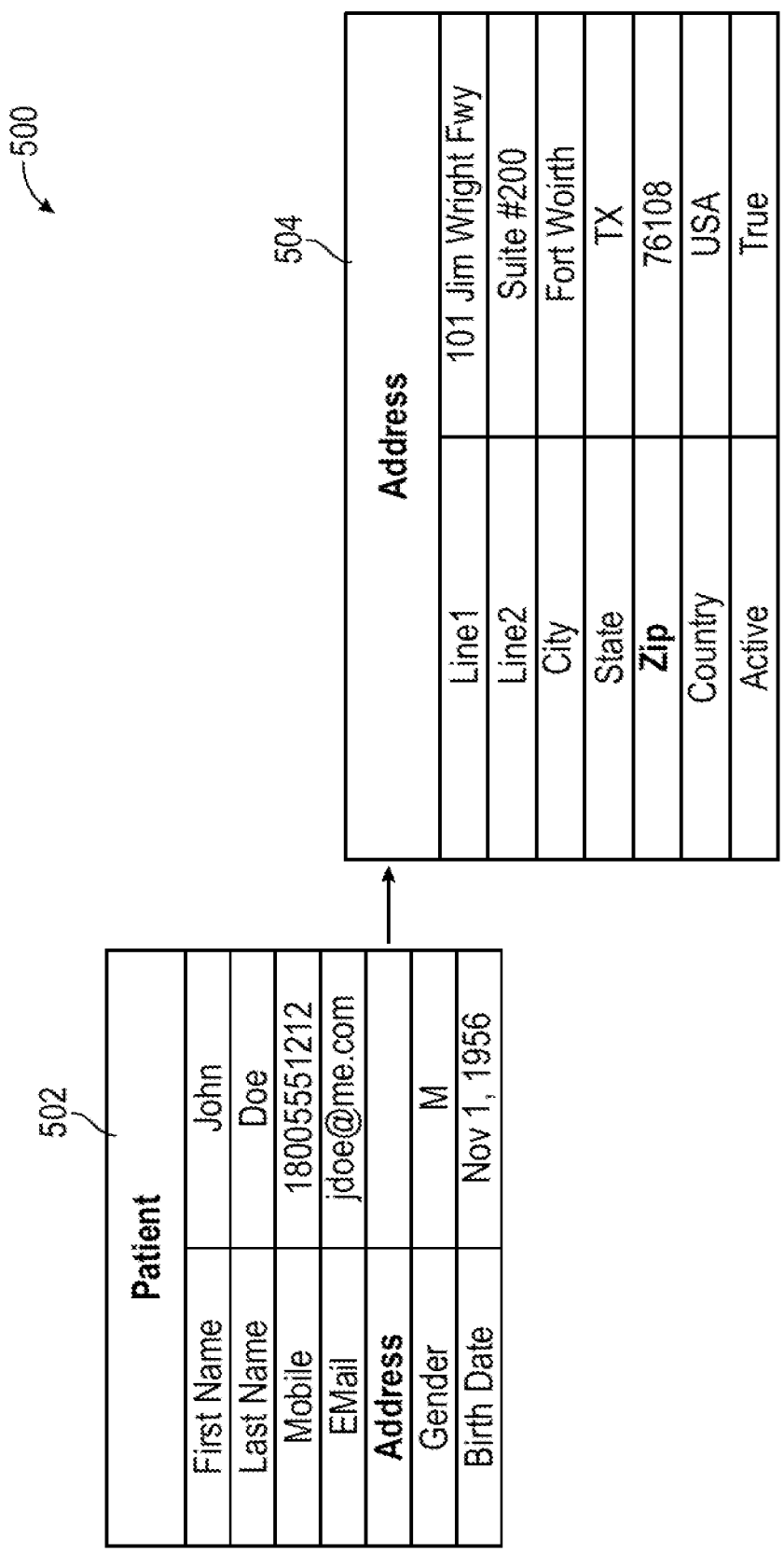
FIG. 5 illustrates a logical diagram of portion of a property collection, in accordance with one or more exemplary embodiments of the present disclosure.

FIG. 5 illustrates a logical diagram of portion of data associated with a property collection, referred to generally as 500, in accordance with one or more exemplary embodiments of the present disclosure. A 'property collection' named 'Patient' 502, can have one or more fields and values associated with the Patient property collection 502. For example, the property collection 502 can include fields such as 'First Name, 'Last Name,' 'Mobile,' 'Email,' 'Address,' 'Gender,' and 'Birthdate,' to name a few. The 'Address' field can be an Address array 504 that can have multiple address entries for a particular patient. For example, the address array entries can include multiple fields such as 'Line 1,' 'Line 2,' 'City,' 'State,' 'Zip,' 'Country,' and 'Active,' to name a few. Address array entries may be the same, have missing information in some entries, or be completely different, based on when the address information was populated.

Figure 6:
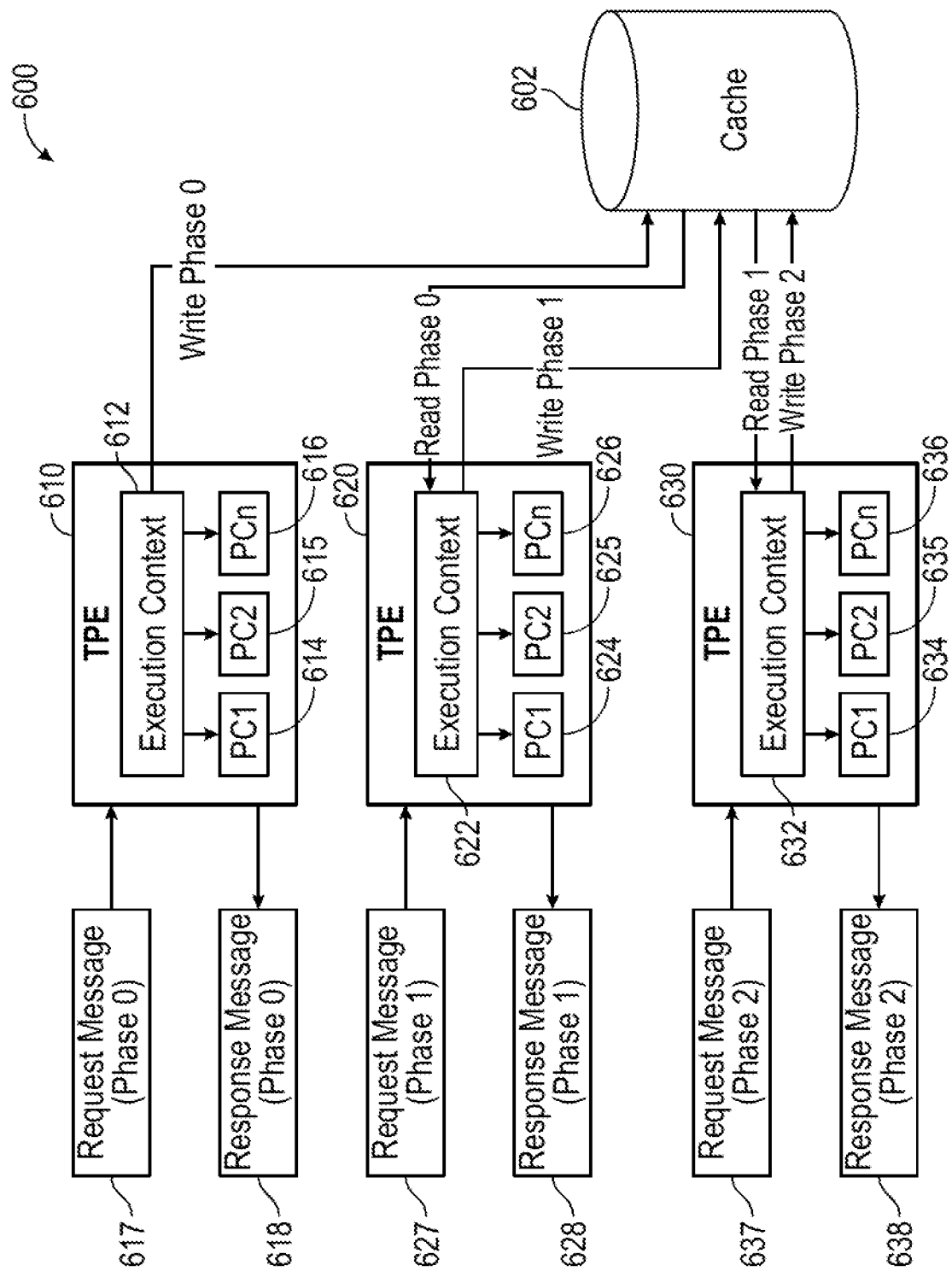
FIG. 6 illustrates a schematic of a transmission processing engine, in accordance with one or more exemplary embodiments of the present disclosure.

FIG. 6 illustrates a schematic of a transmission processing engine (TPE) system 600, in accordance with one or more exemplary embodiments of the present disclosure. The TPE system 600 can include one or more TPEs 610, 620, 630. Each TPE 610, 620, 630 can include an execution context 612, 622, 632, and one or more property collections PC1 614, 624, 634, PC2 615, 625, 635, and PCn 616, 626, 636, where n is a variable for n-number of property collections. The one or more one or more property collections PC1 614, 624, 634, PC2 615, 625, 635, and PCn 616, 626, 636 can be the same, similar, partially similar, or different. Each of the TPEs 610, 620, 630 can be operably coupled to a memory (e.g., cache 602).

In one embodiment, a first TPE 610 can receive a request message 617 with a phase of 0, write a response message 618 with a of phase 0, and write to memory 602 with a write phase of 0. The first TPE 610 can process the request message according to the execution context 612 using the property collections PC1 614, PC2 615, and PCn 616 and write its output to memory 602 using a write phase of 0. In another embodiment, a second TPE 620 can receive a request message 627 with a phase of 1, read from the memory 602 with a read phase of 0, write a response message 628 with a phase of 1, and write to memory 602 with a write phase of 1. The second TPE 620 can process the request message according to the execution context 622 using the property collections PC1 624, PC2 625, and PCn 626 and write its output to memory 602 using a write phase of 1. In another embodiment, a third TPE 630 can receive a request message 637 with a phase of 2, read from the memory 602 with a read phase of 1, write a response message 638 with a phase of 1, and write to memory 602 with a write phase of 2. The third TPE 630 can process the request message 637 according to the execution context 632 using the property collections PC1 634, PC2 635, and PCn 636 and write its output to memory 602 using a write phase of 2. In one embodiment, each TPE 610, 620, 630 can write the 'execution context' to memory 602 (e.g., cache) after each processing phase of a 'transmission' is complete and 'reads' the 'execution context' from cache when the next processing phase of a 'transmission' begins.

Figure 7:
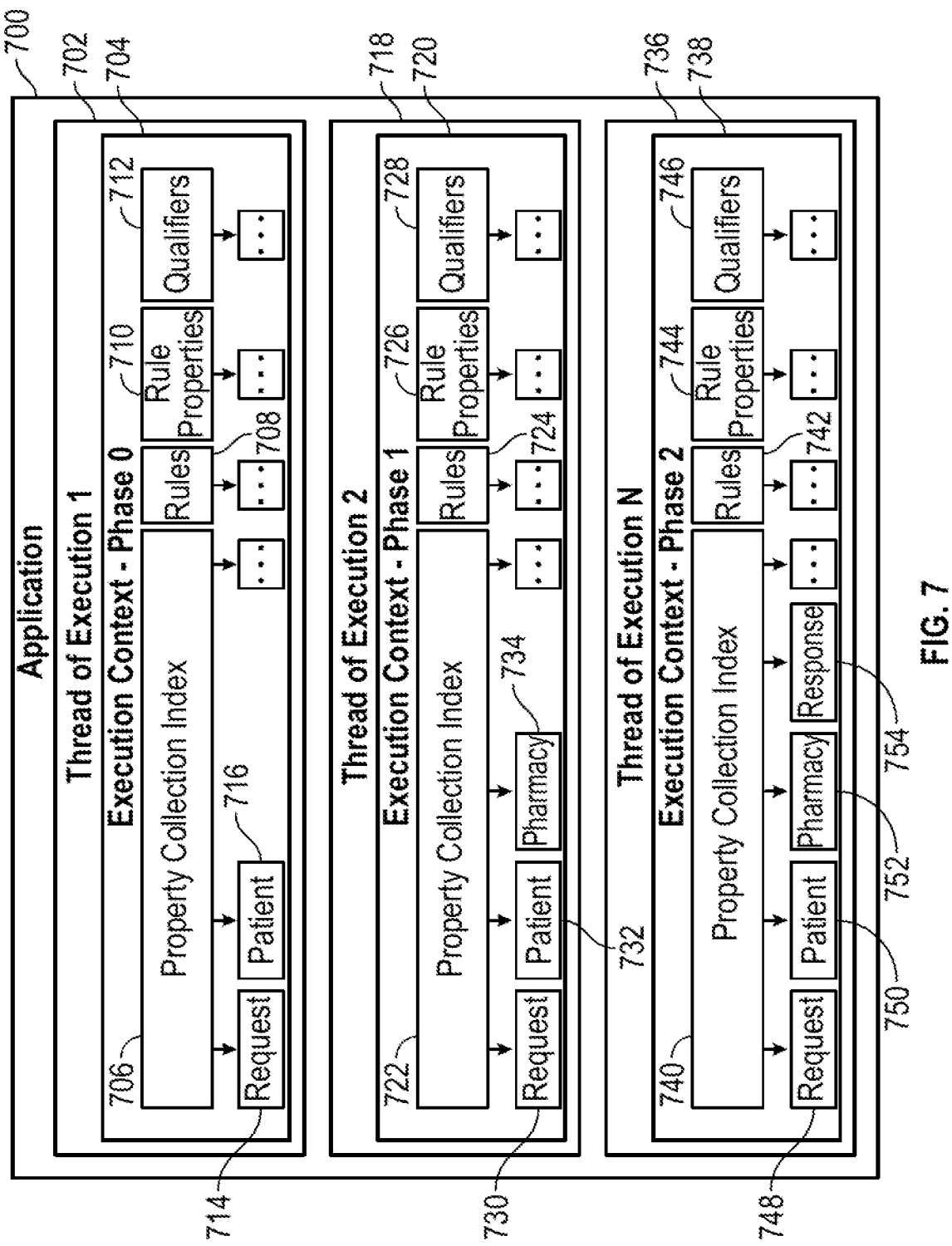
FIG. 7 illustrates a schematic of a multi-threaded application, in accordance with one or more exemplary embodiments of the present disclosure.

FIG. 7 illustrates a schematic of a multi-threaded application 700, in accordance with one or more exemplary embodiments of the present disclosure. The multi-threaded application 700 can include a first thread of execution 702 having an execution context phase of 0 704. The execution context phase 0 704 can include a property collection index 706, one or more rules 708, one or more rule properties 710, and one or more qualifiers 712. The property collection index 706 can include one or more property collections, including request 714 and patient 716. The multi-threaded application 700 can also include a second thread of execution 718 having an execution context phase of 1 720. The execution context phase 1 720 can include a property collection index 722, one or more rules 724, one or more rule properties 726, and one or more qualifiers 728. The property collection index 722 can include one or more property collections, including request 730, patient 732, and pharmacy 734. The multi-threaded application 700 can also include an nth thread of execution 736 having an execution context phase of 2 738. The execution context phase 2 738 can include a property collection index 740, one or more rules 742, one or more rule properties 744, and one or more qualifiers 746. The property collection index 740 can include one or more property collections, including request 748, patient 750, pharmacy 752, and response 754.

In one embodiment, an application can have several active threads of execution, with each thread having its own 'execution context.' Each 'execution context' can also be in a different phase. In another embodiment, the implementation of threads and processes can differ between operating systems, but in most cases a thread can be a component of a process. Multiple threads can exist within one process, executing concurrently and sharing resources such as memory, while different processes do not share these resources. In particular, the threads of a process can share executable code and the values of dynamically allocated variables and non-thread-local global variables at any given time.

In another exemplary embodiment, in operation, when a 'transmission' is received a parser factory object can be instantiated, which determines the type of transmission received. The parser factory can then instantiate a 'parser' associated with the 'transmission type' and stores a reference to the parser in the 'execution context.' The parser can also add a 'Property Collection Interface' to the index of 'Property Collections' created within the execution context. This interface will provide access to the parser's data, using the standard access methods of a 'Property Collection' (e.g., the parser acts like it is a standard 'Property Collection'). The 'name' of the 'Property Collection Interface' can be associated with the type of transmission received.

For example, if the 'transmission type' is a 'request', the name of the 'Property Collection' could be called 'Request'. If the 'transmission type' is a 'response' the 'Property Collection' could be called 'Response'. Once a parser has been created the execution context can load the 'Rules,' 'Rule Properties' and 'Qualifiers' associated with the transmission type.

The execution context can then perform 'Qualification', which will determine the 'Rule Properties' to be used for each 'Rule.' Each 'Rule' can then be executed for each 'Rule Property' associated with the 'Rule'. As a 'Rule' is executed it can choose to load additional data items/entities (e.g., Patient, Pharmacy, etc.) from some kind of persistence media, such as a blockchain, database, cache, etc. Once all rules have been processed, the execution context can send a 'response transmission' back to the client.

Figures 8A, 8B:
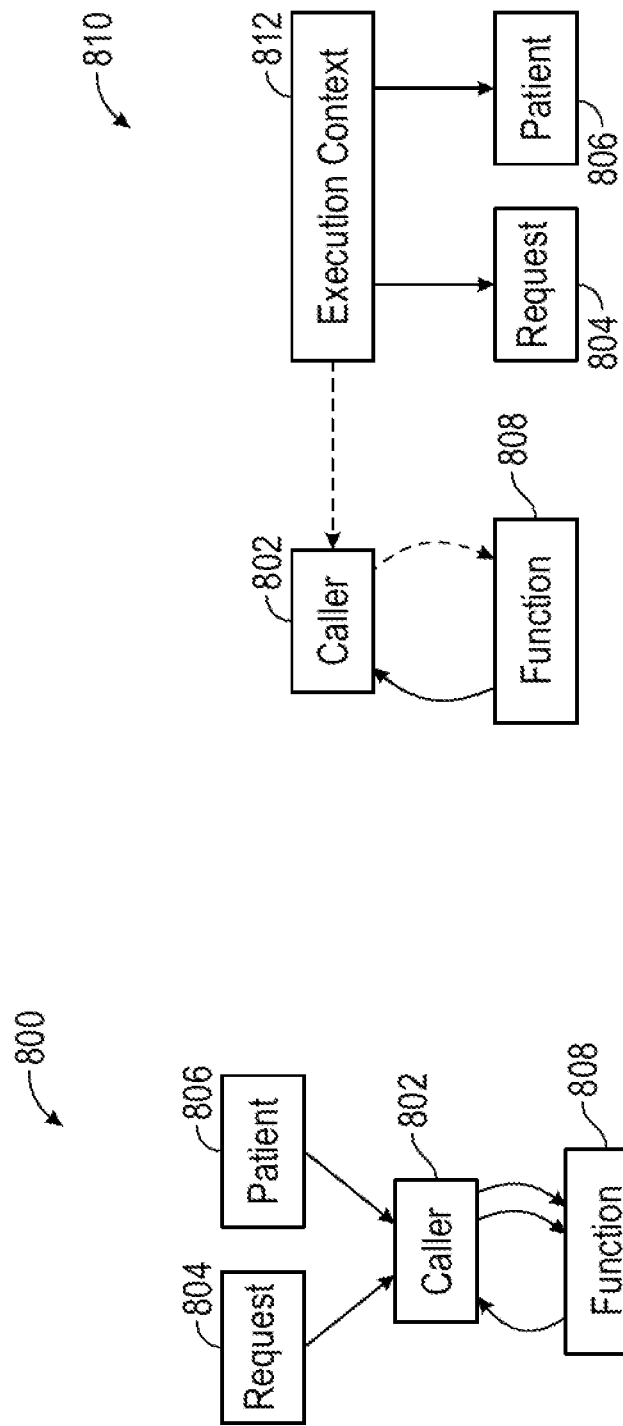
FIGS. 8A and 8B illustrate embodiments of function argument data flows, in accordance with one or more exemplary embodiments of the present disclosure.

FIGS. 8A and 8B illustrate embodiments of function argument data flows, in accordance with one or more exemplary embodiments of the present disclosure. Referring to FIG. 8a, a typical programming paradigm 800 is to pass information to methods/functions as arguments. This requires that the code calling the function gather all the data required by the function and then pass that data to the function using the arguments of the function.

The arguments position, name, and data type, for a specific method/function form what is known as the method/function signature. The calling program must know about the signature of the method/function to be called. This results in a tight coupling between the caller of the function and the function.

Function Arguments Example

| Function definition: |
| --- |
| decimal DetermineTotalPrice<br>(decimal drugCost, decimal fillFee)<br>{<br>   return   drugCost  +  fillFee;<br>} |

| Function caller: |
| --- |
| decimal  drugCost  =  50.23;<br>decimal  fillFee  =  5.50;<br>decimal  totalPrice  =  DetermineTotalPrice<br>(drugCost,  fillFee); |

Referring to FIG. 8B, the execution function programming paradigm 810, solves the problems of the typical programming paradigm 800, by passing the 'function' a reference to an 'execution context' and have the function retrieve the data items it needs through the 'execution context.' This approach allows the function itself to be in control of the data items that it needs. If the function requirements change, only the function changes and not the code calling the function. The 'function' can use a method on the 'execution context' to retrieve each required data item using an XPP. In another embodiment, all 'Property Collections' that exist in the execution context can be available to the function.

In another embodiment, a 'Dynamic Function' is a function that can be loaded at runtime and reloaded if and when a new version of the function becomes available. A 'Dynamic Function' can be designed to be called with only one argument, which is a reference to the 'execution context'. This allows the function to at least:

Read any data items that it needs using an XPP;
Write any data item that it needs using an XPP;
Create, update, or delete 'Property Collections;' and
Call all supported 'methods' on the 'execution context.'

One benefit of the application execution environment is how these pieces of technology interact with each other through a common 'language' and 'process methodology.' The 'language' can be the data addressing and access methodology of the 'execution context' and an 'XPP.' The 'process methodology' can use an 'execution context' object as the manager of one or more 'Property Collections,' such that all data can be created, updated, loaded, and deleted by the application. The 'execution context' can also manage the loading of 'business logic' in the form of 'Rules' and context associated 'Rule Property' data through a process of 'Qualification.' The 'Qualification' process can load 'Qualification Functions' and 'Qualification Lists,' which have access to all data within the 'execution context' and use an XPP to access that data. A 'Qualification List' can use the retrieved data to compare against a predefined list of data to determine if there is a match. A 'Qualification Function' can use the retrieved data, in conjunction with logic, to determine qualification.

Persons skilled in the art will readily understand that advantages and objectives described above would not be possible without the particular combination of computer hardware and other structural components and mechanisms assembled in this inventive system and described herein. Additionally, the algorithms, methods, and processes disclosed herein improve and transform any general-purpose computer or processor disclosed in this specification and drawings into a special purpose computer programmed to perform the disclosed algorithms, methods, and processes to achieve the aforementioned functionality, advantages, and objectives. It will be further understood that a variety of programming tools, known to persons skilled in the art, are available for generating and implementing the features and operations described in the foregoing. Moreover, the particular choice of programming tool(s) may be governed by the specific objectives and constraints placed on the implementation selected for realizing the concepts set forth herein and in the appended claims.

The description in this patent document should not be read as implying that any particular element, step, or function can be an essential or critical element that must be included in the claim scope. Also, none of the claims can be intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim can be understood and intended to refer to structures known to those skilled in the relevant art, as further modified or enhanced by the features of the claims themselves, and can be not intended to invoke 35 U.S.C. § 112(f). Even under the broadest reasonable interpretation, in light of this paragraph of this specification, the claims are not intended to invoke 35 U.S.C. § 112(f) absent the specific language described above.

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the inventions can be established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

What is claimed is:

1. A system for managing data using an execution context, comprising;
a memory storing one or more property collections;
and a computer processor operably coupled to the memory and capable of executing machine-readable instructions to perform program steps, the program steps comprising:
receiving input data from a client, the input data having an input data format with data fields and respective data field values;
instantiating a first thread;
instantiating an execution context configured to change processing logic and data requirements of functions at runtime by passing a function a reference to an object and having the function retrieve the data items needed, in the first thread:
parsing the input data using an input parser based on the input data format:
storing the parsed data in a first property collection in a standardized format to provide access to the parsed data;
loading rules, rule properties, and qualifiers based upon the input data;
qualifying the rules and rule properties to determine which rule properties to use for each rule;
executing the rules against one or more stored property collections to generate output data;
storing the output data in an output property collection;
wherein the execution context addresses data using an execution context property path (XPP); and
wherein the XPP includes a modifier to append additional information to and XPP request.

2. The system of claim 1, wherein an input parser factory determines the input parser format based on the input data format.

3. The system of claim 2, wherein the input data is received from the client via a listener configured to instantiate the input parser factory.

4. The system of claim 1, further comprising instantiating an output parser to format the output data in the input data format.

5. The system of claim 4, wherein the output parser factory determines the output parser format based on the input data format.

6. The system of claim 1, further comprising transmitting the output data in the input data format to a client.

7. The system of claim 6, wherein a responder transmits the output data in the input data format to a client using the same manner of transmission.

8. The system of claim 1, wherein the XPP is an ACSII string.

9. A method for managing data using an execution context, comprising;
receiving input data from a client, the input data having an input data format with data fields and respective data field values;
instantiating a first thread;
instantiating an execution context configured to change processing logic and data requirements of functions at runtime by passing a function a reference to an object and having the function retrieve the data items needed, in the first thread:
parsing the input data using an input parser based on the input data format:
storing the parsed data in a first property collection in a standardized format to provide access to the parsed data;
loading rules, rule properties, and qualifiers based upon the input data;

qualifying the rules and rule properties to determine which rule properties to use for each rule;

executing the rules against one or more stored property collections to generate output data:

storing the output data in an output property collection;

wherein the execution context addresses data using an execution context property path (XPP); and wherein the XPP includes a modifier to append additional information to and XPP request.

10. The method of claim 9, wherein an input parser factory determines the input parser format based on the input data format.

11. The method of claim 10, wherein the input data is received from the client via a listener configured to instantiate the input parser factory.

12. The method of claim 9, further comprising instantiating an output parser to format the output data in the input data format.

13. The method of claim 12, wherein the output parser factory determines the output parser format based on the input data format.

14. The method of claim 9, further comprising transmitting the output data in the input data format to a client.

15. The method of claim 14, wherein a responder transmits the output data in the input data format to a client using the same manner of transmission.

16. The method of claim 9, wherein the XPP is an ASCII string.

* * * * *